(12) United States Patent
Swoboda (10) Patent No.: US 8,067,216 B2
(45) Date of Patent: Nov. 29, 2011

(54) METHOD FOR MACERATING BIOLOGICAL MATERIAL AND APPARATUS FOR CARRYING OUT SAID METHOD

(75) Inventor: Werner Swoboda, Boeblingen (DE)

(73) Assignees: Eisenmann Anlagenbau GmbH & Co. KG (DE); Forschungszentrum Karlsruhe (DE)

( * ) Notice: Subject to any disclaimer, the term of this patent is extended or adjusted under 35 U.S.C. 154(b) by 895 days.

(21) Appl. No.: 11/709,584

(22) Filed: Feb. 22, 2007

(65) Prior Publication Data

US 2007/0202601 A1 Aug. 30, 2007

(30) Foreign Application Priority Data

Feb. 24, 2006 (DE) .................... 10 2006 009 157

(51) Int. Cl.
*C12N 13/00* (2006.01)

(52) U.S. Cl. ............... 435/173.6; 435/173.4; 435/173.7

(58) Field of Classification Search ............... 435/173.4, 435/173.6, 173.7
See application file for complete search history.

(56) References Cited

U.S. PATENT DOCUMENTS

| | | | | |
|---|---|---|---|---|
| 5,643,742 | A * | 7/1997 | Malin et al. ................. | 435/29 |
| 6,043,066 | A * | 3/2000 | Mangano et al. .......... | 435/173.7 |
| 6,074,605 | A * | 6/2000 | Meserol et al. ............. | 422/33 |
| 2002/0137121 | A1 * | 9/2002 | Rubinsky et al. ............... | 435/29 |
| 2003/0011386 | A1 * | 1/2003 | Xie et al. ...................... | 324/694 |
| 2004/0084381 | A1 * | 5/2004 | Korenev ....................... | 210/748 |

FOREIGN PATENT DOCUMENTS

DE 10144486 4/2003

OTHER PUBLICATIONS

H. Bluhm, W. Frey, C. Gusbeth, M. Sack and C. Schultheiss, IHM, "Aufschluss und Abtötung biologischer Zellen mit Hilfe starker gepulster elektrischer Felder" in Nachrichten des Forschungszentrums Karlsruhe, vol. 35, issue 3, 2003, pp. 105 to 100.

* cited by examiner

*Primary Examiner* — Leon B Lankford
*Assistant Examiner* — Susan E Fernandez
(74) *Attorney, Agent, or Firm* — Factor Intellectual Property Law Group, Ltd.

(57) ABSTRACT

In order to ensure consistently good maceration of biological material in an electroporation reactor, it is proposed to monitor the conductivity of the mixture therein and to detect any arcing which occurs therein. The results of such monitoring are used to modify the operating voltage of the electroporation reactor and/or the composition of the mixture located in the reactor channel.

18 Claims, 6 Drawing Sheets

METHOD FOR MACERATING BIOLOGICAL MATERIAL AND APPARATUS FOR CARRYING OUT SAID METHOD

RELATED APPLICATIONS

The present invention claims the benefit of the filing date of German Patent Application, Serial No. 10 2006 009 157.4, filed Feb. 24, 2006; the content of which is incorporated by reference herein.

TECHNICAL FIELD

The present invention is directed to biological material and more specifically, toward a method and apparatus for macerating biological material.

BACKGROUND OF THE INVENTION

Naturally occurring active ingredients which serve as therapeutic agents, nutritional supplements, aromas, fragrances, colours etc., or other domestically or industrially usable substances, are often located in the cells of biological materials. These biological materials are made up of cells, each of which comprises a cell membrane enclosing the cell contents.

In order to gain access to the various active ingredients, which are present not only in the cell contents but also in the cell membrane itself, the cell membrane must be opened. Mechanical methods are in particular used for this purpose to destroy the cell membrane. Physical methods (for example boiling), chemical methods and biological methods (inter alia fermentation) are also known for releasing active ingredients.

Active ingredient should here be taken to mean not only an active ingredient in the narrow pharmacological sense, but also any substance which is of economic interest (by its presence or absence).

Recently, electroporation has also been used for opening cell membranes. Electroporation is, however, limited to those biological materials which comprise cells containing water and/or oil.

In comparison with the above-mentioned known cell maceration methods, electroporation achieves maceration in a gentler and more effective manner.

Occasionally, when treating a macroscopically uniform mixture in electroporation reactors, breakdowns may occur, in which the entirety or a large proportion of the applied high voltage is dissipated through a thin discharge channel. A large proportion of the material accordingly remains untreated by this high voltage pulse. The discharge channel created by breakdown or parts of the channel and any residual discharge products may furthermore constitute nuclei for further breakdowns.

Changes in the conductivity of the material to be treated may also impair the efficiency of electroporation.

The present invention is provided to solve these and other problems.

SUMMARY OF THE INVENTION

An object of the present invention is to achieve further improvement in the maceration of cells by countering the above-stated disruptive influences.

This object is achieved according to one embodiment of the present invention directed a method for macerating biological material, in which the biological material is dispersed in a carrier medium and the mixture of carrier material and biological material is treated by electroporation. An occurrence of electrical breakdowns is monitored during the electroporation treatment and at least one parameter of the electroporation treatment is controlled as a function of the result of the monitoring.

The breakdowns may be identified in simple manner with light-responsive detectors and detected by means of the pressure pulses generated in the mixture.

If breakdowns occur in the electroporated mixture, these may also be identified from the amplitude and time profile of the current pulses. The energy typically stored in a capacitor is dissipated very much faster in the event of a breakdown.

Additionally, breakdowns may be particularly straightforwardly detected by monitoring the width of the current pulse through the electroporation reactor or of the high voltage pulse decaying at the mixture.

A still further embodiment of the present invention permits ongoing monitoring of conductivity, i.e., even in treatment phases in which no arcing is occurring. In this way, it is also possible to identify and detect those cases in which electrical conductivity is too low and no arcing may occur. In such a case, the conductivity of the mixture may be increased in order to reestablish conditions which are favourable for electroporation. This further development also makes it possible to counter incipient conductivity outliers right from the outset.

In a further embodiment of the present inventino, the conductivity of the mixture of carrier medium and biological material is monitored and at least one parameter of the electroporation treatment is controlled as a function of the result of conductivity monitoring.

It yet another further embodiment of the present invention directed to macerating biological material, in which the biological material is subjected to a pretreatment, the pretreated biological material is dispersed in a carrier medium, and the mixture of carrier material and biological material is treated by electroporation; the conductivity of the mixture of carrier material and biological material is monitored and at least one operating parameter of the pretreatment is controlled as a function of the result of conductivity monitoring.

These embodiments of the present invention are based on the concept that it is favourable to carry out electroporation under operating parameters which ensure consistently good efficiency of the poration produced by the field pulses.

Put simply, the present invention makes it possible to identify when the field strength used for electroporation is too high or the material treated does not contain sufficiently puncture-proof non-uniformities.

In practice, the composition of the mixture of carrier medium and biological material often varies. For example, when macerating grapes, there may be batches having a different level of ripeness and a different sugar content. Depending on how far ripening has progressed, the cell walls exhibit different levels of mechanical stability. It is accordingly convenient to adjust the level of field pulses used. On the other hand, excessively strong field pulses may result in breakdowns in the electroporation reactor, which means that a field pulse which gives rise to a breakdown does not contribute to electroporation of the cells.

In a further embodiment of the present invention, the conductivity of the mixture of biological material and carrier medium is monitored and at least one parameter of the electroporation treatment and/or of a pretreatment of the biological material is modified as a function of the measured conductivity.

In a still further embodiment of the present invention, a deviation in the conductivity of the mixture from the desired nominal value is identified even before electroporation. This permits particularly rapid correction during pretreatment or mixing of the biological material with the carrier medium.

Various control parameters for electroporation include the electrical field strength which is maintained during electroporation, the length of the field pulses which are used during electroporation, the spacing of the field pulses which are used during electroporation, and the total number of field pulses which are used during electroporation. Any of these parameters may initially be modified—in the event of any deviation in conductivity—to reestablish trouble-free operation of electroporation; until, once conductivity has been readjusted to its nominal value, which can be achieved only slowly. Additionally, the direct operating parameters of electroporation can be reset to their normal values.

Other control parameters include the temperature of the mixture while electroporation is carried out, the pressure to which the mixture is exposed during electroporation, and the duration of the electroporation treatment; which make it possible to return electroporation conditions to those conditions under which electroporation runs smoothly with a time constant which is small in comparison with the correction of conductivity.

Additional control parameters, which make it possible to return the conductivity of the mixture to its nominal value, include the ratio between biological material and carrier material in the mixture, and the intensity of a pretreatment—in particular pre-comminution of the biological material.

Control parameters that are advantageous on pretreatment of biological material containing little or no liquid—requiring liquid to be introduced into the interior of the cells in a pretreatment in order to reestablish a weak conductivity therein—include treatment time, the nature and quantity of added penetration liquid, the temperature at which the pretreatment is carried out, the pressure at which the pretreatment is carried out, and the nature and the intensity with which the mixture of biological material and penetration liquid is moved during pretreatment.

Control parameters involved in modifying the conductivity of the mixture of carrier medium and biological material in the context of a pre-treatment include the nature and concentration of the pretreatment agent, the temperature of the pretreatment, the intensity of the pretreatment, or the movement of the biological material during pretreatment.

It is also possible to control the conductivity of the mixture by modifying the recirculation rate of material from one method step to a preceding method step such that the control parameter is the quantity of the recirculated material stream. If, in so doing, the recirculated material stream is subjected to an intermediate treatment, the treatment may include the intensity of the intermediate treatment, the duration of the intermediate treatment, or the nature or concentration of auxiliary substances used during the intermediate treatment, such as to enable the adjustment of the conductivity of the mixture supplied to the electroporation reactor.

Various mechanisms by which transient reductions in the efficiency of electroporation may be offset and a consistent result achieved in the electroporated material include the reducing the conveying speed of the mixture, shortening the spacing between successive field pulses, or reducing the height or width of the the field pulses. Similarly, mechanisms by which transient increase in the efficiency of electroporation may be offset and a consistent result achieved in the electroporated material include the increasing the conveying speed of the mixture, lengthenin the spacing between successive field pulses, or increasing the height or width of the the field pulses.

In some cases it may be necessary, if severe disruption in electrical conductivity occurs, which may be recognised from a spate of breakdowns, to take an emergency measure in order to protect the installation and/or the treated material. Such measures include switching off the electrical field for a predetermined period of time or permanently, rapid ejection of the volume of mixture which is just being subjected to electroporation from the electroporation reactor, and error stop of the installation. In addition, an emergency measure may also be initiated immediately upon occurrence of the first breakdown. Preferable emergency measures include, and are not limited to, switching off the electrical field for a predetermined period of time or permanently, rapid ejection of the volume of mixture which is just being subjected to electroporation from the electroporation reactor, and error stop of the installation In those cases in which the conductivity of the mixture is (partially) controlled by addition of an auxiliary component, conductivity may rapidly be returned to its nominal value, wherein an additive which influences conductivity is additionally added to the mixture, such that the controlled parameter is the quantity of the added additive—before it is subsequently ensured by means of a modification to the pretreatment or by means of another mixture of the biological material to be treated with carrier medium that the desired conductivity of the mixture is obtained even without conductivity additive or with the normal quantity thereof.

An additional embodiment of the present invention capable of carrying out one or more of the embodiments disclosed herein may be embodied using conventional commercial sensors and circuits and includes an electroporation reactor which comprises two electrodes which at least in part define a treatment channel, which electrodes are connected to a high voltage pulse generator, wherein a breakdown detection device is provided which comprises one or more devices/means from the following group: a current sensor with an amplitude discriminator or pulse width discriminator acted upon by said current sensor; a light detection device which is in optical connection with the treatment chamber; a pressure sensing device which is in pressure connection with the treatment chamber; an acoustic sensor which is in acoustic connection with the treatment channel. Such and apparatus is capable of providing a signal which is characteristic of the current conductivity of the mixture—e.g., via a conductivity measurement device which cooperates with the mixture in the interior of the treatment channel or with the mixture located upstream of treatment channel.

Before exemplary embodiments of the invention are described in detail, some general points relating to the performance of the invention will first be addressed, making reference to the more complex case of macerating biological material with a low liquid content. The simpler case of macerating biological material, the cells of which already obtain sufficient liquid, proceeds mutatis mutandis by omitting the liquid enrichment step.

Many biological materials containing active ingredients scarcely contain any, or no longer contain, water in their cells. These are, for example, dried plant parts or plant parts having only a low water content from the outset, for example barks, certain plant roots or fir or mountain pine needles etc.

According to the present invention, in a first method step, a penetration medium is initially supplied to the biological material with a low fluid content, which penetration medium is incorporated into the cells, and, in a second method step, the cell walls of the biological material enriched with penetration medium are dispersed in a carrier medium and destroyed by electroporation.

Liquid and gaseous penetration media may in particular be considered. They generally have the function of adjusting the electrical conductivity of the cells to a value which is within the conductivity range of living cells with a high liquid content, for example that of the leaves of broad-leaved trees, lettuce and fruit. In practice, this means a conductivity of a mash produced from the latter-stated materials of approx. 0.1 mS/cm to approx 100 mS/cm, usually between approx 0.5 mS/cm and 30 mS/cm.

Herein disclosed, a biological material should be taken to mean any material in which cell contents are enclosed by a cell wall. These may comprise both eukaryotic materials (such as plant materials) and prokaryotic cells.

These materials differ not inconsiderably with regard to the size of their cells. At a smaller cell diameter, a correspondingly higher electrical field strength is used during electroporation, in order to achieve a voltage drop over the individual cells in the range from approx. 0.5 V to approx 2 V.

Media usable to establish or reestablish conductivity in biological cells are designated penetration media within this disclosure, since they penetrate into the interior of the cell through the cell walls or defective portions thereof.

These primarily comprise liquids and gases (in particular vapours) with appropriate electrical properties.

Since many cells containing little or no water contain salts, it is often sufficient to introduce ordinary water or water vapour into the cells in order to bring about electrical conductivity therein.

Suitable penetration liquids include not only water, but also aqueous solutions, for example isotonic salt solutions or comparable biologically active solutions. It is, however, also possible to use other liquids or gases which are not normally found in cells which exhibit similar electrical conductivity provided that they are taken up into the cells of the biological material in a liquid pretreatment step.

In the method according to the invention, the cells of the biological material enriched with penetration medium are introduced in a carrier medium into an alternating electrical field, as is typically used for electroporation.

Suitable carrier media have weak electrical conductivity. This should be taken to mean a conductivity which is not substantially better than, preferably is poorer than, the conductivity of the cells, so that the current pulses flowing during electroporation do not bypass the cells.

Typical conductivity values for good carrier media are therefore of the order of a few mS/cm.

Another fundamental property of the carrier media is their dielectric strength in the electrical fields used for electroporation (typically 1 kV/cm up to 100 kV/cm).

An electroporation field comprises a plurality of successive narrow and tall field pulses, the strength of the field being selected such that pre-existing small pores and/or ion channels in the cell walls are enlarged or new pores are created in the cell walls.

Weakly conductive water is in particular suitable as carrier liquid. Weakly conductive should in this connection be taken to mean water which is of typical drinking water quality or of elevated process water quality, i.e. water with a conductivity of 0.1 mS/cm to approx. 10 mS/cm.

Instead of water, it is however also possible to use other liquids, provided that they exhibit the appropriate electrical properties which ensure that potential differences of the order of magnitude of 0.5 V to 2 V are achieved at opposing peripheral zones of the individual cells of the material to be macerated.

Biological material may be macerated not only with the objective of extracting a useful active ingredient after the maceration, but also with the objective of eliminating an unwanted contaminant from the macerated material, for example an unwanted bitter substance or the like in a foodstuff.

The electroporation used according to the invention is indeed per se known in conjunction with biological materials containing water, as shown in the paper by Bluhm, Frey et al. in Nachrichten des Forschungszentrums Karlsruhe, volume 35, issue 3, 2003, pages 105 to 110. DE 10144486 C1 also discloses the maceration and pasteurisation of organic material by electroporation, taking sugar beet by way of example.

However, as explained above, these known methods are not suitable for those biological materials which have a low liquid content.

Moreover, no measures are taken therein to counter the occurrence of breakdowns.

In contrast, it is possible by means of the present invention to achieve gentle and highly effective maceration of the cells, even with problematic materials.

This is achieved at a low energy input (in comparison with thermal methods) and with slight heating of the biological material and thus in gentle manner. Yield is improved on extraction of active ingredients and contaminants in an extraction step following maceration. Treatment time is shortened. Maceration also proceeds substantially simultaneously and thus homogeneously throughout the entire volume.

BRIEF DESCRIPTION OF THE DRAWINGS

The invention is explained in greater detail below by means of exemplary embodiments with reference to drawings in which.

DETAILED DESCRIPTION OF THE INVENTION

While this invention is susceptible of embodiment in many different forms, there is shown in the drawings and will herein be described in detail one or more embodiments with the understanding that the present disclosure is to be considered as an exemplification of the principles of the invention and is not intended to limit the invention to the embodiments illustrated.

Figure 1:
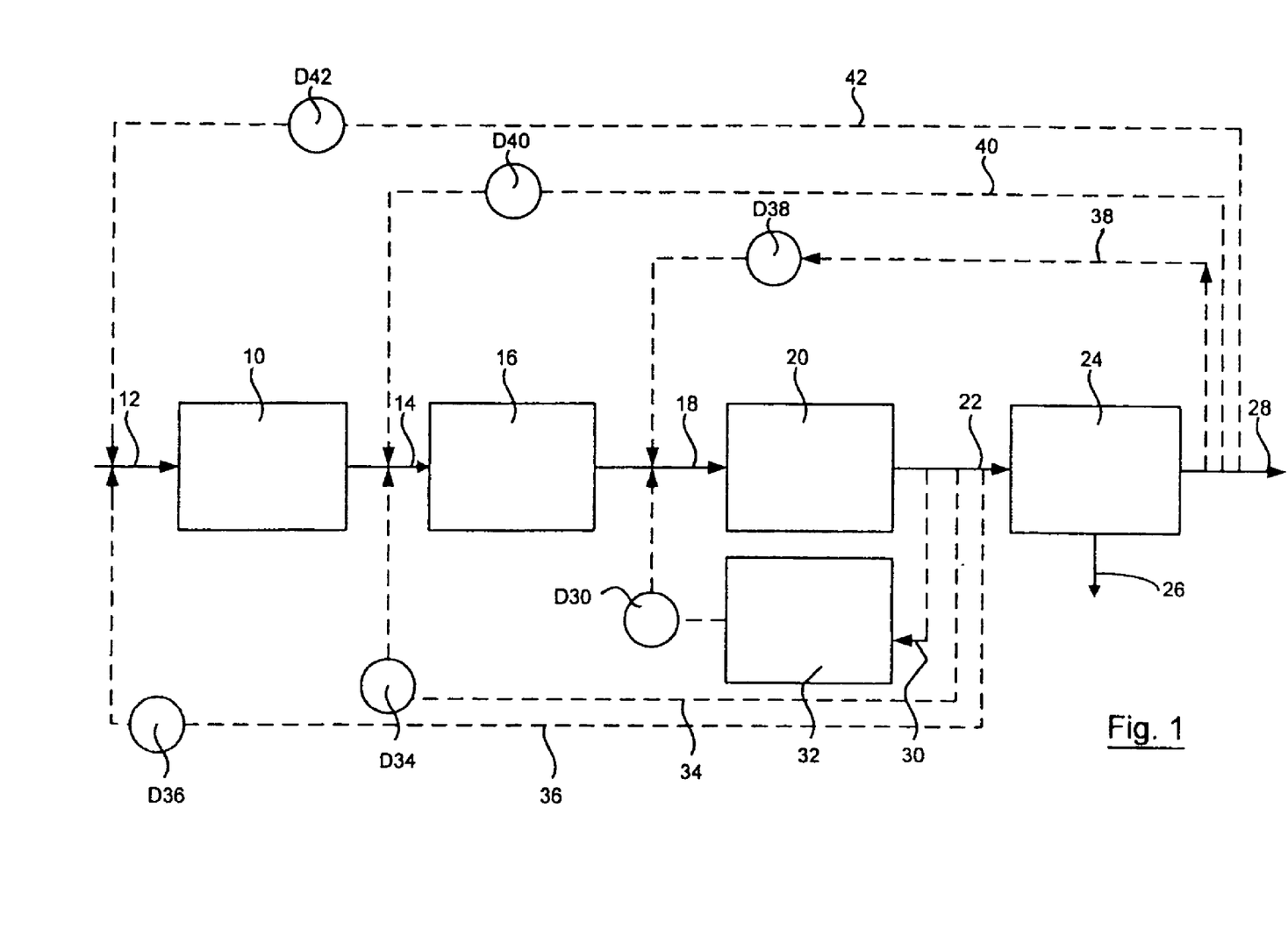
FIG. 1: shows a schematic diagram of a method according to the invention for macerating plant material which is dried or contains little water.

A comminution station 10 is supplied according to FIG. 1 with a stream 12 of dry plant material to be macerated. This material may comprise dried lime blossom, dried peppermint or other dried blossoms or leaves of medicinal plants. It may, however, also comprise other dried plant parts, for example dried plant roots (for example restharrow roots). The plant material may also be of a type which from the outset contains only very little liquid, for example bark, wood, fruit stones/pips, seeds or the like.

The comminution station 10 may comprise means for cutting, chopping, grinding, crushing or pressing the plant material. A stream of comminuted plant material is indicated by an arrow 14. This stream is supplied to a pretreatment reactor 16 which contains a weakly conductive liquid, in particular water.

The ground plant material remains in contact with the water for a sufficiently long period in the pretreatment reactor 16, until water has penetrated into the interior of the cells. Said water penetration may be assisted by adjusting the contents of the pretreatment vessel 16 to a temperature which, in the case of an unpressurised pretreatment vessel and using water as the penetration liquid, may be between 5° C. and 95° C.

Alternatively, water may be introduced in the cells of the plant material with superheated steam, a temperature of up to approx. 150° C. being preferred for plant and equipment reason and in order to protect the biological material.

Again with regard to gentle treatment of the plant material and in particular of proteins contained therein, a temperature of the steam of approx. 50° C. to approx. 80° C. is preferred, the pressure of the steam advantageously also being lowered in such a manner that the water boils at the stated temperature. At a temperature of 80° C., this means a pressure of approx. 0.47 bar, at 70° C. a pressure of 0.32 bar and at 50° C. a pressure of 0.12 bar.

It should be noted that the operating temperature and duration of treatment in the pretreatment reactor 16 is selected with regard to promoting the penetration of water into the interior of the cells, but not with regard to leaching active ingredients out of the cells.

After a sufficient residence time in the pretreatment reactor 16, a mash stream, symbolically designated 18, of comminuted biological material, which has been re-enriched with water, and water is transferred into an electroporation reactor 20, where the mash is exposed to a succession of very short elevated field pulses, the size of which is determined such that a voltage drop of approx. 0.5 to 2 V is obtained over a cell.

At cell dimensions in the range from a few μm to a few hundred μm and at conventional plant mash conductivities of a few tens of μS/cm to a few tens of mS/cm, this means generating electrical field strengths in the interior of the electroporation reactor in the range between 1 kV/cm and 100 kV/cm.

Specifically, field strength will be selected as a function of the material to be macerated. It is here also possible to a smaller extent to offset a lack in amplitude of the field pulses by increasing the length of the individual field pulses, so permitting the use of a simpler and less costly pulse generator.

A material stream 22 is thus obtained at the outlet of the electroporation reactor 20 which comprises any residual penetration water, now acting as carrier medium, cell wall envelopes and cell contents.

Optionally after separation of the carrier water, the macerated material stream 22 passes into an extraction station/posttreatment station 24, in which, by using a suitable solvent and/or physical means (mechanical and/or application of pressure and/or heating), the desired active ingredient is dissolved out of the cell contents and/or the cell walls (due to the destruction of the cell walls, substances stored on and/or in these are more readily accessible for extraction).

An extract stream 26 may be drawn off from the extraction station 24, while a residual material stream 28 comprising the carrier water and any unextracted fractions of the material stream 22 is disposed of.

The above-described method may be performed batchwise or continuously, wherein the various reactors are provided with continuously operating rotary sluices or corresponding intermittently actuated valves, which need not be explained in detail here.

Animal material from which active ingredients are to be isolated is often first dried in order to be able to store it for longer before processing or to transport it inexpensively over relatively large distances. It may then be processed in exactly the same manner as has been described above with reference to plant materials.

The above-described method examples were those which involved isolating organic active ingredients from the starting materials. It goes without saying that this method may also equally well be used for isolating inorganic substances from biological material ("leaching").

In the above-described methods, the focus was also on the active ingredients isolated from the starting material. The method according to the invention may, however, also be used as a purification method in which an unwanted soluble contaminant is removed from a starting material. In this case, it is the extract stream 26 which is discarded, while the residual material stream 28 is sent for further utilisation.

Modifications to the above-described method are indicated by broken lines in FIG. 1.

First variations of the method relate to recirculating at least a proportion of the material stream 22 to a preceding method step.

For many materials, it may be advantageous not to effect complete maceration of the material in a single pass through the electroporation reactor 20, as this would then require too much time (and energy). Therefore, according to one variant, the material stream is recirculated on a path 30 via an intermediate treatment station 32 to the inlet of the electroporation reactor 20.

The intermediate treatment 32 may simply involve storing the electroporated material stream in a vessel for a predetermined period of time, during which, starting from the perforations which have already been produced, further swelling creates new points of attack for another electroporation step.

The intermediate treatment may, however, also involve a chemical treatment which, starting from the cell wall defects produced in the first electroporation step, forms new points of attack for a subsequent further electroporation treatment.

Moreover, by allowing a more highly electrically conductive liquid to diffuse into the interior of the cells through the cell wall defects produced in the first electroporation, it is possible during a further electroporation, in which a poorly conducting carrier liquid is still used, to direct the current passing through the reactor more strongly through the interior of the individual cells and so enhance the destruction thereof.

In a further variant, a proportion of the material stream 22 is recirculated via a path 34 to the inlet of the pretreatment reactor 16. In this manner, more complete refilling of the individual cells with liquid is achieved, as this is assisted by the defects produced in the wall by the first electroporation.

Finally, a proportion of the material stream 22 may also be recirculated via a path 36 to the inlet of the comminution station 10 and so exploit the fact during mechanical comminution that the material has already been mechanically weakened during the first electroporation. In this manner, the material may also be very finely comminuted with a low energy input, something which could less readily be achieved with the dry material with intact cell walls.

Further variants of the method shown in FIG. 1 involve recirculating proportions of the residual material stream 28 to preceding stages of the method. Such recirculation is indicated by paths 38, 40, 42, which lead back to the electroporation reactor 20, the enrichment reactor 16 and the comminution station 10 respectively. The advantages obtained in this manner generally involve more thorough maceration, in a similar manner as described for paths 30, 34, 36.

Corresponding flow controllers D30, D34, D36, D3S, D40, D42 are provided to control throughput in paths 30, 34, 36, 38, 40, 42. Specifically, these may take the form of a proportional valve which is moved by a servomotor which is in turn activated by a control system.

In a further modification of the method shown in FIG. 1, intermediate treatments may also be provided in paths 34 to 42 in order to weaken the cell walls further and so enhance separation of the wanted from the unwanted constituents of the biological material.

Figure 2:
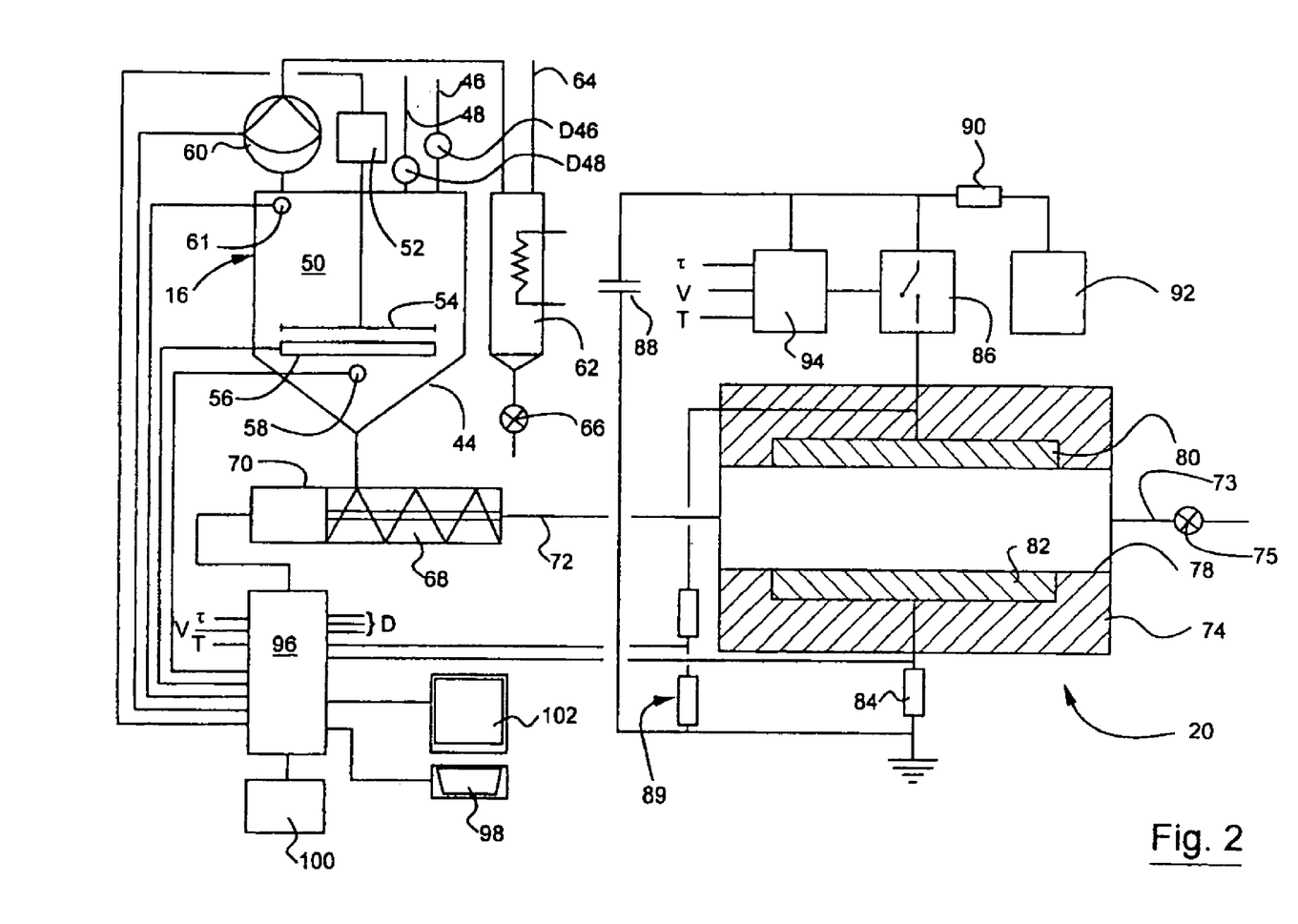
FIG. 2: shows a schematic diagram of an installation for introducing liquid into dried biological material and for electroporating of the biological material which has again been enriched with liquid.

FIG. 2 is a schematic diagram of the details of the pretreatment reactor 16 and of the electroporation reactor 20 and an associated control system.

The pretreatment reactor 16 comprises a vessel 44 with a conical outlet portion, which is sealed in pressure-tight manner and which is supplied via a first line 46 with water and via a second line 48 with the comminuted biological material prepared by the comminution station 10.

Controllable flow controllers D46 and D48 again serve to adjust the material streams in the lines 46 and 48.

In the interior of the vessel 44, a volume 50 of water and comminuted biological material is shown diagrammatically.

An electrical motor 52 is provided in order to rotate a stirrer 54.

A heat-transfer element 56 is provided in the vessel 44 in order to adjust the vessel contents to a temperature differing from ambient temperature which may typically be between approx. 5° C. and approx. 95° C., preferably between approx. 15° C. and approx. 50° C.

The temperature prevailing in the vessel 44 is measured by a temperature sensor 58.

The interior of the vessel 44 is evacuated using a vacuum pump 60, in order to extract any residual air from the mixture of water and ground biological material. A pressure sensor 61 monitors the vacuum in the vessel 44.

The outlet from the vacuum pump 60 is connected via a cold trap 62 with an exhaust air line 64. The condensate which accumulates in the cold trap 62 may be drawn off via a valve 66.

Depending on the biological material used, the condensate may for example comprise highly volatile essential oils which may be put to further use.

The outlet of the vessel 44 is connected to a screw pump 68 which is driven by an electrical motor 70, the rotational speed of which is controllable.

The outlet from the screw pump 68 is connected to the inlet of the electroporation reactor 20 via a line 72. The screw pump 68 here maintains atmospheric pressure or an overpressure, so minimising the amount of arcing brought about by gas inclusions under the electrical fields prevailing in the electroporation reactor 20.

A cellular wheel sluice 75 is provided in the outlet line 73 which discharges the electroporated material in order to adjust the pressure established in the interior of the electroporation reactor 20 by the screw pump 68 to atmospheric pressure (or other subsequent pressure). Alternatively, pressure may be reduced using a throttle, a flow controller or a valve or further increased using another pump.

The electroporation reactor 20 has a housing 74 made from a puncture-proof, insulating and impact resistant material which comprises a flat reaction channel 78 of rectangular cross-section. In practice, the height of the reaction channel 78 may amount to approx. 5 mm to 200 mm, preferably to approx. 40 mm.

Materials which may in particular be considered for the housing 74 are: plastics and fibre-reinforced plastics, in particular transparent or translucent plastics such as polycarbonate; glass, in particular laminated glass; high strength industrial ceramics, optionally also fibre-reinforced.

Electrodes 80, 82 taking the form of metal plates are inserted flush in the upper and lower (in the drawing) boundary surfaces of the reaction channel 78. The plate material preferably comprises (optionally as a coating) stainless steel, titanium or titanium-iridium, noble metal, in particular gold, silver, platinum.

The electrodes 80, 82 are generously rounded at the edges in order to avoid field peaks at these edges.

The lower electrode 82 of the pair is connected to earth via a measuring shunt resistor 84, while the upper electrode 80 is connected via a controllable switch 86 with a capacitor bank, which is shown as a single capacitor 88.

A voltage divider 89 permits measurement of the voltage prevailing at the electrodes 80, 82 and, in conjunction with the current sensor formed by the measuring shunt resistor 84, measurement of electrical power.

The capacitor 88 is charged via a charging resistor 90 by a high voltage charging unit 92. For relatively small electroporation reactors, as may be used in connection with the maceration of medicinal plants, said unit only need supply currents ranging from a few mA up to a few A.

The switch 86 is controlled by a control circuit 94 which receives at two input terminals a signal τ, which specifies the length of a switch pulse, and a signal T, which specifies the time spacing of switch pulses.

In addition, the control circuit 94 may comprise a control terminal V, at which it is possible to specify the voltage at which the switch 86 is to be actuated.

The control signals τ, T and V are provided by a process computer 96. As indicated by a conductor bundle D, the process computer 96 also controls the various flow controllers D which are provided in the lines of the installation, as described above.

Parameters for the biological material to be macerated can be input into the process computer 96 via a keypad 98. On the basis of these parameters and sets of operating parameters assigned thereto, which are held in storage means 100 of the process computer 96, the process computer 96 calculates for the biological material in question the most favourable values for the voltage up to which the capacitor 88 should be charged, for the width τ of the switch pulses and for the spacing T of the switch pulses and for further operating parameters of the electroporation installation including the pretreatment reactor 16 and other components of the installation shown in the Figure.

A monitor 102 serves to display installation operating parameters and to check inputs.

Typical values for τ are approx. 10 ns to approx. 100 μs, preferably approx. 100 ns to approx. 50 μs.

Typical values for 1/T are approx. 0.1 Hz to approx. 500 Hz, preferably approx. 0.2 Hz to approx. 50 Hz, still more preferably approx. 0.5 Hz to approx. 40 Hz.

Every time that the switch 86 is closed by a switch pulse, the capacitor 88 discharges through the mash volume, which is located directly between the two electrodes 80 and 82. When this happens, currents of the order of a few thousand A occur transiently.

Taking account of the electrical conductivity of the mash, these currents generate voltage differences of the order of approx. 2 V between the upper and lower portions of the cell wall. These differences are so large that pre-existing small pores and ion channels in the cell walls are irreversibly widened, so destroying the cell wall.

If the conductivity of the mash is too low, the current which flows through the mash when the switch 86 is closed is too small. Conversely, if the electrical conductivity of the mash is too high, the good conductivity of the mash means that no sufficiently large voltage drop builds up across the individual cells for cell wall destruction to occur.

For this reason, the conductivity of the mash must lie within a specific window, the lower limit of which is at approx. 0.1 mS/cm and the upper limit at approx. 100 mS/cm.

Continuous monitoring of the conductivity of the mash is provided by the measuring shunt resistor 84 which is connected to an input of the process computer 96. Alternatively or additionally, the voltage divider 89 may also be used.

On identifying a change in conductivity, the process computer 96 immediately modifies the voltage to which the capacitor 88 is charged in such a manner that the same voltage drop across a cell is again achieved, so that the cell walls continue reliably to be broken up. However, this measure subjects the high voltage charging unit 92 to heavier loads.

The process computer 96 will therefore simultaneously influence production of the mash (by controlling temperature, stirring and input quantities of biological material and water) such that the electrical conductivity of the mash returns to the normal range. As this is achieved, the charging voltage of the capacitor 88 may then be turned back down to the initial value.

The conveying speed of the cells through the electroporation reactor, which corresponds to the flow velocity of the carrier water, should be adjusted in such a manner that the cells are exposed to a sufficient number of field pulses for the cell walls to be so severely destroyed that active ingredients may be obtained from the contents of the cell or the cell walls in a subsequent treatment step in a desired yield and within a desired extraction time.

The total number of field pulses to which the cell material is exposed in the electroporation reactor 20, the width and frequency of the field pulses and their height, the temperature during electroporation and the operating parameters during preparation of the mash (degree of comminution of the dry biological material, mixing ratio with water, any pretreatment additives used, temperature during pretreatment, duration of pretreatment, intermediate storage times) are in each case determined experimentally for a specific material which is to be macerated for a specific purpose and held in the storage means 100 for retrieval via the keypad 93. The basis for this may be parameters which have previously been determined for cells which are similar in terms of cell size and composition.

By way of modification of the above-described exemplary embodiment, the switch 86 may also be replaced by a gas discharge gap. This exploits the characteristic of a gas discharge gap that it breaks down on application of a predetermined voltage. This breakdown voltage may be controlled by means of the pressure of the gas enclosed in the gas discharge gap. Pressure control of the gas discharge gap thus in effect replaces the control circuit 94.

Figure 3:
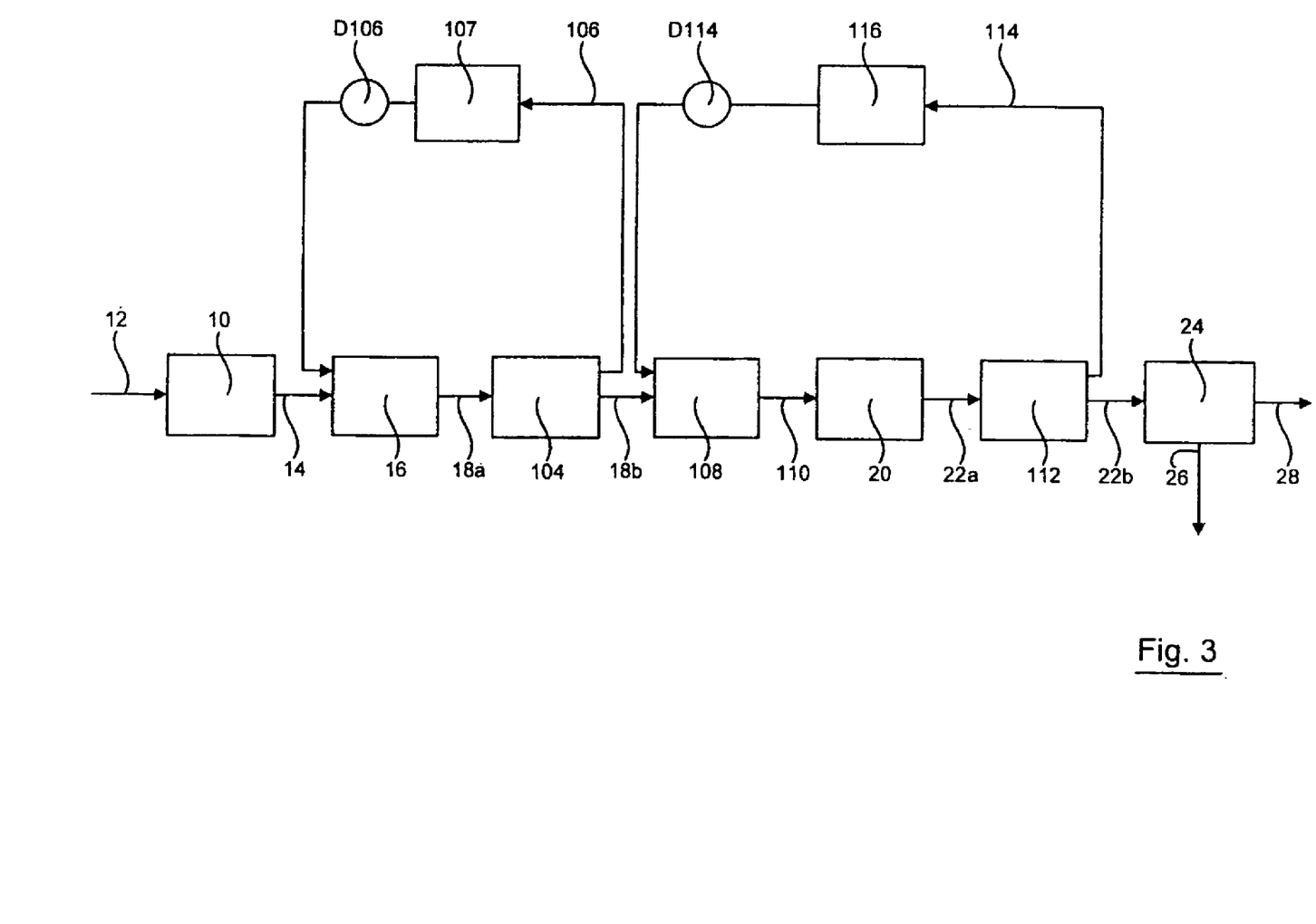
FIG. 3: shows a similar diagram to FIG. 1, but illustrating a modified method.

The method illustrated in FIG. 3 differs from that in FIG. 1 in that conductivity is reestablished in the interior of the cells by using a penetration liquid which differs from the carrier liquid which serves to carry the cells through the electroporation reactor.

Components of the installation shown in FIG. 3 which have already been discussed with reference to FIG. 1 are assigned the same reference numerals and need not be described in detail again. The different variants for product recirculation in the process are also omitted from FIG. 3 for clarity's sake. It goes without saying that recirculation paths corresponding to paths 30, 34, 36, 38, 40 and 42 of FIG. 1 may also be provided in the installation according to FIG. 3.

The installation according to FIG. 3 differs from that according to FIG. 1 in that a separate carrier liquid stream is used to carry the particles of the biomaterial to be macerated through the electroporation reactor 20.

In particular, the penetration liquid used may be water to which conductivity-raising substances, in particular salts, are added, while normal tap water with lower conductivity or deionised or distilled water is used as the carrier liquid.

The carrier liquid may also be such a liquid which is immiscible with the penetration liquid used in the pretreatment reactor 16. Water or an aqueous solution is preferably used in the pretreatment reactor 16. Such a penetration liquid is generally capable of penetrating cell walls effectively, it optionally being possible to incorporate a surface-active substance in order to attack wax or fat layers borne on the cell surfaces. In this case, a conductive oil within the stated conductivity range of 0.1 mS/cm to 10 mS/cm is used as a water-immiscible carrier liquid.

Gases may also be considered as carrier medium, provided that they are weakly conductive and puncture-proof, the stream here passes vertically through the electroporation reactor 20 in order to avoid gravity segregation of carrier medium and biological material. The same applies to upstream and downstream parts of the installation.

A separation stage 104, which separates off the penetration liquid which has not been absorbed by the biological material, is connected to the output of the pretreatment reactor 16. The separation stage 104 may be, for example, a filter or a centrifuge. The penetration liquid separated therein may be recirculated into the pretreatment reactor 16 via a line 106, which may contain a regeneration unit 107.

A controllable flow controller D106, which may be of a similar structure to the flow controllers described with reference to the above Figures, determines the size of the material stream in the line 106.

A stream 18b of biological material re-enriched with liquid, which corresponds to the mash stream 18a but contains only little penetration liquid is supplied to the inlet of a mixing stage 108, the other inlet of which receives the carrier medium. A material stream 110 of carrier medium and biomaterial, the cells of which are refilled with water, is obtained at the output of the mixing stage 108.

The material stream 110 then passes through the electroporation reactor 20, the cell walls of the material again being destroyed by the sharp and elevated field pulses.

The material stream 22 obtained at the output of the electroporation reactor 20 is then passed into a further separation stage 112, in which the carrier medium, on the one hand, and the destroyed cells of the biological material, on the other hand, are separated from one another. Known physical methods, for example filtration or centrifugation, may again be used for this purpose.

The carrier medium is recirculated back to the mixing stage 108 via a line 114 and a regeneration stage 116, while the stream of cell walls and cell contents is supplied to the extraction station 24.

A controllable flow controller D114 determines how much mixture is recirculated via the line 114.

In this way it is possible to establish different conductivities in the carrier medium and in the interior of the cells to be destroyed in such a manner that the current flowing between the electrodes of electroporation station preferably flows through the cells where they are available.

Figure 4:
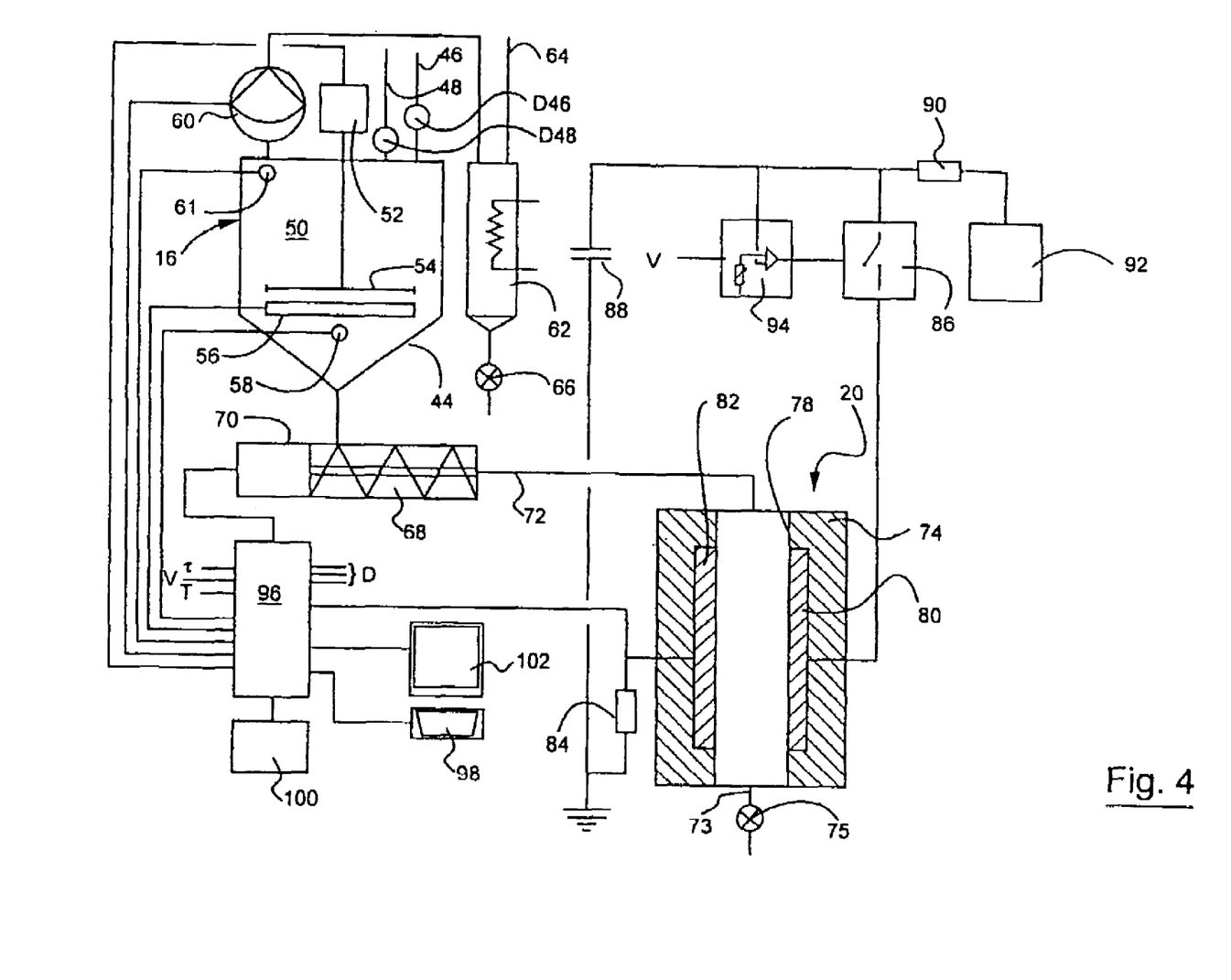
FIG. 4: shows a similar diagram to FIG. 2, but in which the electroporation reactor is oriented vertically and a modified high voltage switching means is used.

In the exemplary embodiment according to FIG. 4, which is very similar to that according to FIG. 2, the electroporation reactor 20 is set up with a vertical orientation of the treatment channel 78.

In the exemplary embodiment according to FIG. 4, the switch 86 is switched by a control circuit 94 which operates as a function of the voltage at the capacitor 88. The control circuit 94 is shown diagrammatically as a comparator with adjustable reference voltage V.

In the exemplary embodiment according to FIG. 4, when the voltage at the capacitor 88 reaches a predetermined value, the control circuit 94 closes the switch 86, and the charge stored in the capacitor flows as a pulse via the electrodes 80, 82, the mixture located therebetween and the measuring shunt resistor 84 to earth. The switch 86 is then re-opened and the capacitor 88 is charged again by the charging unit 92 via the charging resistor 90. The entire arrangement thus operates as a high voltage pulse generator.

Figure 5:
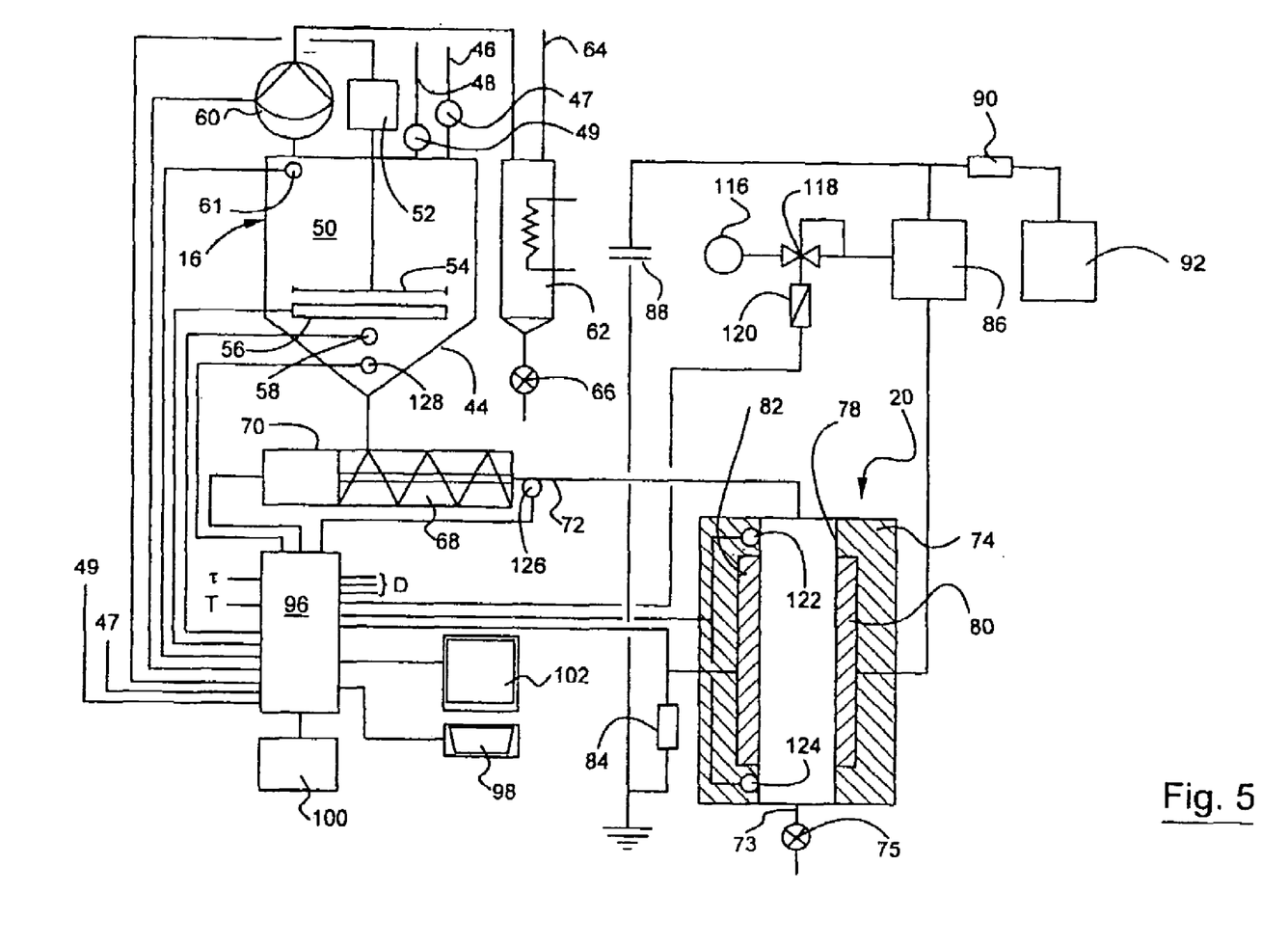
FIG. 5: shows a similar view to FIG. 4, but showing a further modified high voltage switching means.

In the exemplary embodiment according to FIG. 5, the switch 86 is replaced by a discharge gap 86'. This breaks down whenever the voltage at its electrodes exceeds a predetermined value. The breakdown voltage depends on nature of the gas located in the breakdown gap 86' and on the pressure thereof.

To this end, a storage vessel 116, which contains a supply of the operating gas used in the breakdown gap 86', is provided. The outlet of the storage vessel 116 is connected via a controllable pressure controller 118 to the breakdown gap 86', the adjustable closing force being illustrated by an electromagnet 120 which is supplied with current from the process computer 96.

In a further modification, a light detector 122, and a pressure sensor (or microphone) 124 are provided in the housing 74 of the installation according to FIG. 5, the output signals of which are combined OR-wise and applied to an input of the process computer 96.

When a breakdown occurs in the reaction channel 78, the corresponding flash of light or the corresponding pressure or acoustic wave is recorded by the detectors 122, 124, and the process computer 96 may then provide a remedy, as is described in greater detail below.

Finally, in the installation according to FIG. 5, a conductivity sensor 126, which is connected to the process computer 96, is provided at the outlet of the screw pump 68.

A further conductivity sensor 128 may be provided in the interior of the vessel 44.

Figure 6:
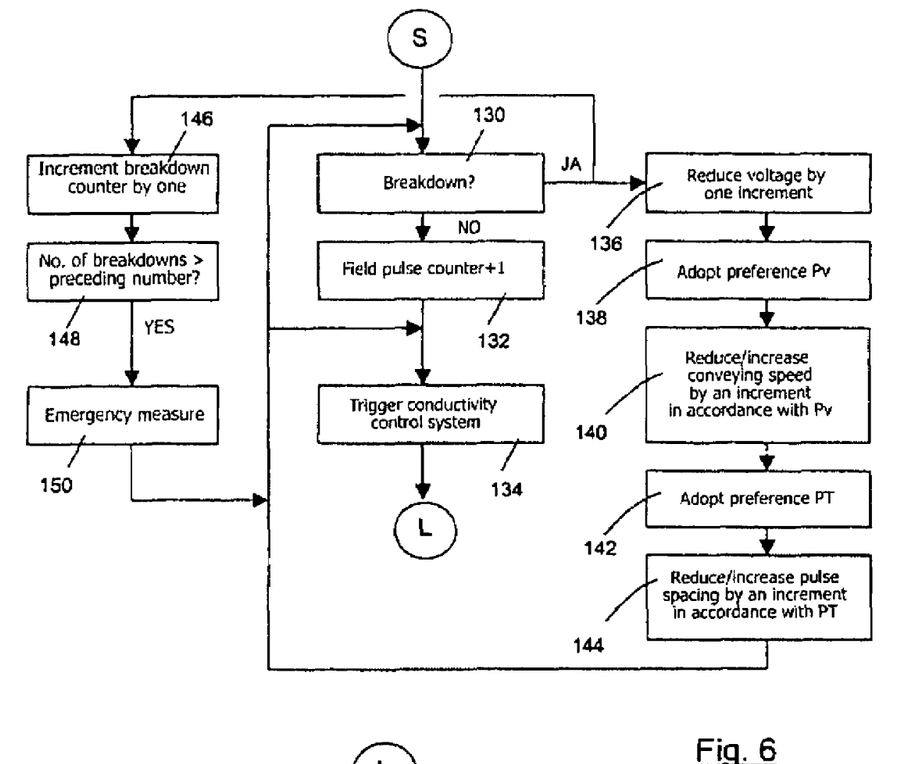
FIG. 6: shows a block diagram of a main routine in accordance with which a computer adjusts the conductivity of the mixture of carrier medium and biological material conveyed through the electroporation reactor; and, FIG. 7: shows a subroutine of the main routine shown in FIG. 6.
Figure 7:
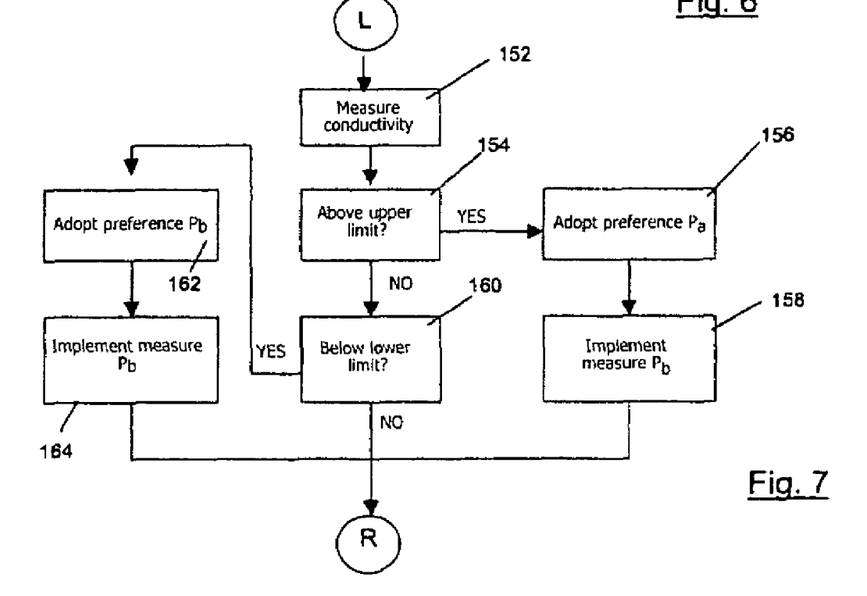

The operation of the process computer 96, to the extent that it serves to maintain consistently good operating conditions in the electroporation reactor 20, will now be outlined with reference to FIGS. 6 and 7.

To this end, the process computer 96 monitors, on the one hand, the conductivity of the mixture of carrier medium and biological material from the vessel 44 to the interior of the reaction channel 78 (where it is monitored by measuring the current pulses running through the measuring shunt resistor 84).

The process computer 96 moreover monitors whether arcing is occurring in the interior of the reaction channel 78. This may be achieved by means of the light pulses falling on the light sensor 122, by means of pressure pulses or acoustic pulses reaching the pressure sensor or the microphone 124, and also by means of the width of the current pulses flowing through the measuring shunt resistor 84, and/or the voltage pulses supplied by the voltage divider 89.

In principle, a main routine of the process computer 96 operates in two stages of differing priority: breakdown monitoring (higher-level) and conductivity control (lower-level).

The process computer 96 here operates timed by pulses which also serve to drive the control circuit 94 or are derived from the voltage decaying at the measuring shunt resistor 84 and/or the output voltage of the voltage divider 89.

It is first checked in a block 130 whether the particular applied voltage has led to a breakdown.

If this is not the case, a field pulse counter (block 132) is incremented by one. The conductivity control system, which is shown in greater detail in FIG. 7, is then triggered (block 134).

If a breakdown is identified, the voltage to which the capacitor 88 is charged or at which the switch 86 is closed is first reduced in a block 136. This may proceed by modifying the reference signal for the control circuit 94 or the current supplied to the electromagnet 120. Each time a breakdown occurs, the voltage is reduced by a predetermined increment which experience has shown is sufficient to reduce the occurrence of a breakdown during a following field pulse.

In a following step in a block 138, a preference value Pv for the further procedure is adopted from a higher-level program element. This serves to select from a plurality of measures, which may likewise serve to avoid the occurrence of a breakdown in the reactor channel 78.

These may include briefly increasing the conveying speed v the mixture in order to discharge a highly conductive, non-homogeneous zone of the mixture out of the electroporation reactor before the next high voltage pulse is applied. If the higher-level program can recognise that it was probably a single breakdown, the higher-level program may on the contrary deem it helpful to reduce the conveying speed so that the material located in the reactor channel 78 is exposed to an additional high voltage pulse and will thus, on leaving the electroporation reactor, have undergone the standard number of pulses.

After the change of conveying speed (or retention of conveying speed) which proceeded in block 140, in a further block 142 a further preference value PT is adopted from a higher-level program which specifies whether the spacing T at which the next high voltage pulse is applied to the flow reactor 20 is provided faster or more slowly. This modification of the pulse spacing proceeds in block 144.

From here, the main routine returns to its starting point S.

If a breakdown is identified, a breakdown counter is simultaneously incremented by one in block 146. This is reset at regular intervals by another program element, as indicated by a reset terminal R.

It is ascertained in a block 148 whether the state of the breakdown counter is greater than a predetermined number (1, 2, 3, etc.). If this is the case, an emergency measure is taken in block 150.

This will then be selected from the following group: alarm and/or error stop of the entire installation; suppression of further high voltage pulses for a predetermined time; rapid reduction in conductivity of the mixture located in the reactor channel 78 by rapidly supplying a relatively large quantity of pure water; rapid ejection of the contents of the reactor channel 78.

FIG. 7 shows a subprogram used by the process computer 96 to maintain the conductivity of the mixture located in the reactor channel 78 within a predetermined conductivity range, which is predetermined by an upper limit and a lower limit.

Continuous conductivity measurement in the reactor channel 78 proceeds in a block 152.

In a further block 164, it is checked whether the instantaneous conductivity is too high. If this is the case, a preference value Pa for a remedial measure to be implemented is adopted in a block 156. An assigned measure is then implemented in block 158 in accordance with this preference value. This may involve reducing the proportion of biological material in the mixture, reducing the intensity of any pretreatment, reducing the addition of a conductive additive or adding more carrier water.

If it is ascertained in block 154 that conductivity is not too high, it is checked in a block 160 whether conductivity is too low.

If this is the case, a preference value Pb, which specifies which of a plurality of provided remedial measures is to be taken, is again adopted from a higher-level program element in a block 162.

This measure may be selected from the following group: increasing the proportion of biological material in the mixture, more intense pretreatment of the biological material, addition of a conductive additive, reduction in quantity of carrier water.

The corresponding measure is then implemented in a block 154.

Similar control loops may run continuously on the basis of the output value of the conductivity meter 126 and the conductivity meter 128.

If the installation has partial recirculation of quantities of material, the correct conductivity may also be established in the reactor channel 78 by suitably modifying the size of the recirculated material streams.

With regard to the avoidance of breakdowns in the electroporation reactor, it is advantageous to avoid therein any operating conditions which could result in the formation of gas or vapour bubbles. This also means that a higher pressure will be established in the electroporation reactor than in upstream treatment reactors and that a temperature will also be established in the electroporation reactor which is higher than in the upstream treatment reactors.

Likewise, with regard to the avoidance of breakdowns, care will be taken during pretreatment of the biological material that said material contains no points or that any points present are blunted.

Extraction of the active ingredients or contaminants may then again proceed in the extraction stage 24 in the manner described further above.

The extraction stage is not restricted to the use of extracting solvents. Physical extraction methods, for example operating on the basis of the action of pressure or temperature, may also be used.

In many products, it may also be of interest in a further modification of the invention to redry a product, from which unwanted substances have been removed, downstream of the extraction stage 24. As a product again having a low liquid content, it is also suitable for long-term storage without any multiplication of microorganisms in the product. However, the treated product still has the characteristic that it comprises numerous channels and free surfaces formed during electroporation which at a later point in time permit rapid exchange of active ingredients with a liquid or a gas.

The above-described method could, for example, be used to treat coffee beans which may be used more economically because the flavour substances and caffeine may be transferred more completely into the water.

Typical examples of biological materials with a low fluid content which may be macerated with the above-described method include precursors for the perfume industry (rose petals, lavender leaves etc.), precursors for pharmacy products (fir needle oil, needles of mountain pine etc.), precursors for the pharmaceuticals industry (for example leaves of medicinal plants (eucalyptus, peppermint, melissa, stinging nettle, lime blossom), barks etc. containing active ingredients and also roots, leaves and fruits of pharmaceutical plants (restharrow root, deadly nightshade, foxglove etc.) and precursors for the food industry (spices, dried fruit, lentils, peas etc.).

Typical examples of animal biological materials are for example meat (for obtaining meat extract) and tissues for isolating hormones (adrenal cortex parts) etc.

The following Examples provide an overview of operating parameters of the electroporation reactor which are suitable together with certain plant materials.

EXAMPLE 1

Production of Restharrow Extract

Restharrow roots were mechanically comminuted into pieces approx. 5 mm in diameter.

The resultant chopped root pieces were combined with water in the ratio 1:3 to yield a mash solution.

The mash solution was stirred for 10 minutes at 19° C.

In this manner, a pretreated mash solution is obtained having an electrical conductivity of 5.9 mS/cm.

This mash solution was placed in an electroporation reactor, the rectangular, mutually facing electrodes of which were spaced 20 mm apart and had edge lengths of 4 cm and 13 cm.

The mash solution was treated with 15 field pulses at a field strength of 12.5 kV/cm. Their length was 2 µs.

Immediately after electroporation, a mash conductivity of 6.9 mS/cm was measured.

Once the mash had stood for 3 hours after electroporation, the water was poured away and the root extract pressed and filtered.

Its conductivity was 10.45 mS/cm.

The residue after pressing was 6.15%.

EXAMPLE 2

Production of Lime Blossom Extract

Lime blossoms with a diameter of 5 to 10 mm were combined with water in the ratio 1:2 to yield a mash solution.

The mash solution was stirred for 10 minutes at 19° C.

In this manner, a pretreated mash solution is obtained having an electrical conductivity of 3.3 mS/cm.

This mash solution was placed in an electroporation reactor, the rectangular, mutually facing electrodes of which were spaced 20 mm apart and had edge lengths of 4 cm and 13 cm.

The mash solution was treated with 15 field pulses at a field strength of 11.5 kV/cm. The length of the field pulses was 2 µs.

Immediately after electroporation, a mash conductivity of 4.68 mS/cm was measured.

Once the mash had stood for 3 hours after electroporation, the water was poured away and the extract pressed and filtered.

Its conductivity was 7.0 mS/cm.

The residue after pressing of the extract was 3.84%.

It should be emphasized that the above-described embodiments of the present invention, particularly, any "preferred" embodiments, are possible examples of implementations merely set forth for a clear understanding of the principles of the invention. Many variations and modifications may be made to the above-described embodiments of the invention without substantially departing from the spirit and principles of the invention. All such modifications are intended to be included herein within the scope of this disclosure and the present invention, and protected by the following claims.

The invention claimed is:

1. A method for macerating biological material, comprising:
dispersing the biological material in a carrier medium to form a mixture;
treating the mixture of carrier medium and biological material by electroporation until pre-existing small pores and ion channels in cell walls of the biological material are irreversibly widened and the cell walls are destroyed;
monitoring for an occurrence of breakdowns in the biological material during the electroporation, wherein breakdowns are formations of thin discharge channels through which the applied voltage can dissipate; and,
controlling at least one parameter of the electroporation treatment as a function of the monitoring.

2. The method of claim 1, wherein the occurrence of breakdowns are monitored by means of light arising from the breakdowns.

3. The method of claim 1, wherein the occurrence of breakdowns is monitored by means of pressure pulses arising from the breakdowns and/or sound arising from the breakdowns.

4. The method according of claim 1, wherein the breakdowns are monitored by means of current pulses flowing through the mixture during electroporation and/or by means of voltage pulses decaying at the mixture.

5. The method according to claim 4, wherein an amplitude and/or a length of the current pulses flowing during electroporation and/or of the voltage pulses decaying at the mixture are monitored.

6. The method of claim 1, further comprising monitoring a conductivity of the mixture by means of a current flowing through the mixture during electroporation and/or a voltage decaying at the mixture.

7. The method according of claim 1, wherein the at least one controlled parameter is selected from the following group consisting of: an electrical field strength which is maintained during electroporation; a length of the electrical field pulses which are used during electroporation; a spacing of the electrical field pulses which are used during electroporation; and, a total number of electrical field pulses which are used during electroporation.

8. A method for macerating biological material, comprising:
dispersing the biological material in a carrier medium to form a mixture; and
treating the mixture of carrier medium and biological material by electroporation until pre-existing small pores and ion channels in cell walls of the biological material are irreversibly widened and the cell walls are destroyed;
monitoring for an occurrence of breakdowns in the biological material during the electroporation, wherein breakdowns are formations of thin discharge channels through which the applied voltage can dissipate;
monitoring a conductivity of the mixture of carrier medium and biological material; and,
controlling at least one parameter of the electroporation treatment as a function of the conductivity monitoring.

9. The method according to claim 8, wherein the at least one controlled parameter is selected from the following group consisting of: an electrical field strength which is maintained during electroporation, a length of the electrical field pulses which are used during electroporation, a spacing of the electrical field pulses which are used during electroporation, and a total number of electrical field pulses which are used during electroporation.

10. A method for macerating biological material, comprising:
subjecting a first biological material to a pretreatment;
dispersing the first pretreated biological material in a carrier medium to form a mixture;
treating the mixture of carrier medium and first pretreated biological material by electroporation until pre-existing small pores and ion channels in cell walls of the first pretreated biological material are irreversibly widened and the cell walls destroyed;
monitoring for an occurrence of breakdowns in the first pretreated biological material during the electroporation, wherein breakdowns are formations of thin discharge channels through which the applied voltage can dissipate;
monitoring a conductivity of the mixture of carrier material and first pretreated biological material; and,
controlling at least one operating parameter of a pretreatment of a second biological material as a function of the conductivity monitoring of the first biological material.

11. The method of claim 10, wherein the conductivity of the mixture is measured before electroporation.

12. The method of claim 10, wherein at least one controlled parameter is the ratio between the biological material and the carrier medium in the mixture.

13. The method of claim 10, wherein the at least one controlled parameter is an intensity of the pretreatment.

14. The method of claim 10, wherein the biological material is a biological material including little or no liquid to which a penetration liquid is supplied in a pretreatment, wherein the penetration liquid imparts a weak conductivity to cells of the biological material, and wherein the at least one controlled parameter is selected from the group consisting of: a treatment time, a nature of the penetration liquid, a quantity of the penetration liquid, a temperature at which the pretreatment is carried out, a pressure at which the pretreatment is carried out, a nature with which the mixture of biological material and penetration liquid is moved during pretreatment and, an intensity with which the mixture of biological material and penetration liquid is moved during pretreatment.

15. The method of claim 10, wherein the pretreatment is selected from the group consisting of: a mechanical pretreatment, a chemical pretreatment with a pretreatment agent, a physical pretreatment, and further wherein the at least one controlled parameter is selected from the following group consisting of: a nature the pretreatment agent, a concentration of the pretreatment agent, a temperature of the pretreatment, an intensity of the pretreatment, and a movement of the biological material during pretreatment.

16. The method of claim 10, wherein when a change in the at least one controlled parameter reduces an intensity of the electroporation treatment and/or reduces a conveying speed of the mixture.

17. The method of claim 10, wherein when a change in the at least one controlled parameter increases an intensity of the electroporation treatment and/or increases a conveying speed of the mixture.

18. The method of claim 10, wherein when a predetermined number of breakdowns are detected within a predetermined time interval an emergency measure is taken,
   wherein the predetermined number of breakdowns is a number greater than a maximum number of breakdowns, and
   wherein the emergency measure is selected from the following group consisting of: switching off an electrical field for a predetermined period of time or permanently; rapid ejection of the mixture which is just being subjected to electroporation from an electroporation reactor; and, an error stop of the device performing the electroporation.

* * * * *